(12) United States Patent
Cigaina

(10) Patent No.: US 6,889,076 B2
(45) Date of Patent: May 3, 2005

(54) DEVICE AND PROCEDURE FOR CONTROLLING THE EXTENT OF INTRA-ABDOMINAL FAT IN THE MONITORING OF AN INDIVIDUAL'S SLIMMING

(75) Inventor: Valerio Cigaina, Villorba (IT)

(73) Assignee: Transneuronix, Inc., Mt. Arlington, NJ (US)

( * ) Notice: Subject to any disclaimer, the term of this patent is extended or adjusted under 35 U.S.C. 154(b) by 224 days.

(21) Appl. No.: 10/112,600

(22) Filed: Mar. 28, 2002

(65) Prior Publication Data

US 2002/0156393 A1 Oct. 24, 2002

(30) Foreign Application Priority Data

Mar. 30, 2001 (IT) .................................... MI2001A0684

(51) Int. Cl.[7] ................................................ A61B 5/00
(52) U.S. Cl. .......................... 600/547; 607/40; 607/133
(58) Field of Search ................................ 600/442, 547; 607/40, 133

(56) References Cited

U.S. PATENT DOCUMENTS

| | | | | |
|---|---|---|---|---|
| 5,335,667 A | * | 8/1994 | Cha et al. .................... | 600/547 |
| 5,449,000 A | * | 9/1995 | Libke et al. ................. | 600/547 |
| 5,833,625 A | * | 11/1998 | Essen-Moller .............. | 600/547 |
| 6,285,898 B1 | * | 9/2001 | Ben-Haim ................... | 600/374 |

FOREIGN PATENT DOCUMENTS

EP          1-063-500 A1 * 12/2000    ............ A61B/5/05

* cited by examiner

Primary Examiner—Eric F. Winakur
Assistant Examiner—Matthew Kremer
(74) Attorney, Agent, or Firm—Fitch, Even, Tabin & Flannery

(57) ABSTRACT

The device (1) for controlling the extent of intra-abdominal fat in the monitoring of an individual's slimming, comprises one electrical signal generator (2) connected to at least one first pole (3), associable to the stomach surface, and a second pole (4), associable to the abdominal wall. The poles (3,4) are connected to detection means (6) and means (7) for processing said electrical signals, adapted to provide a signal indicating the extent of intra-abdominal fat. The control procedure of the entity of the intra-abdominal fat in the monitoring of an individual's slimming, consists in detecting the impedance of the abdominal fat tissues, and hence, in calculating the extent of intra-abdominal fat is obtained.

7 Claims, 1 Drawing Sheet

Figure 1:
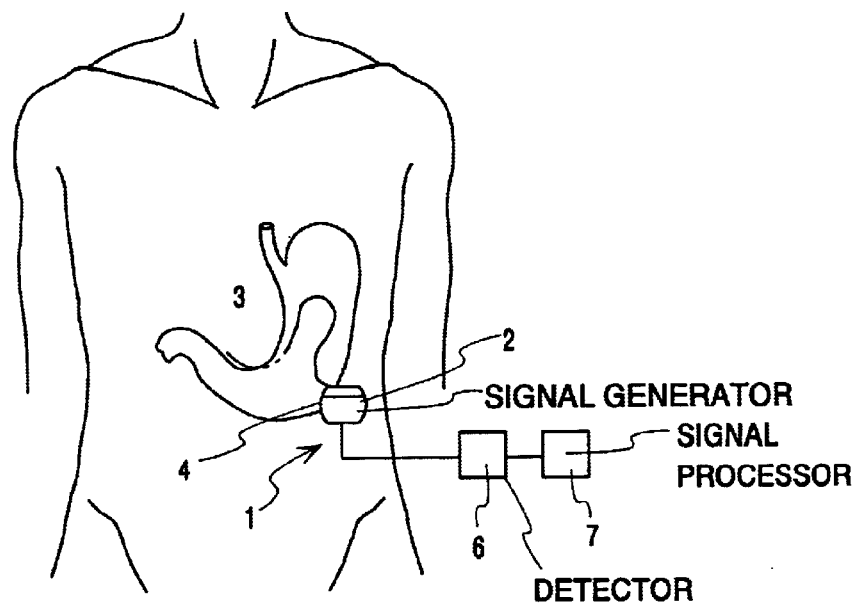

DEVICE AND PROCEDURE FOR CONTROLLING THE EXTENT OF INTRA-ABDOMINAL FAT IN THE MONITORING OF AN INDIVIDUAL'S SLIMMING

FIELD OF THE INVENTION

The present invention relates to a device and a method for controlling the extent of intra-abdominal fat in the monitoring of an individual's slimming program.

BACKGROUND OF THE INVENTION

The measurement of intra-abdominal fat extent has an important prognostic value on the patient's health, since obesity causes several and frequent vascular conditions.

At present, the evaluation of intra-abdominal fat in the monitoring of slimming after a bariatric surgical procedure or an implant of a gastric stimulator (pacemaker) is based on empirical, radiological or ultrasound procedures.

However, the information regarding the intra-abdominal fat obtained by traditional methods does not allow frequent checks. It therefore does not allow keeping the progressive patient's slimming under control.

Moreover, the evaluation of the intra-abdominal fat according to traditional procedures, requires complex instruments (in particular radiological ones, but also ultrasound ones) and in some cases, traditional control operations must necessarily carried out in a very restricted number due to the possible harmful effects for the patient (in particular with radiological methods).

OBJECTS OF THE INVENTION

The principal object of the present invention is to eliminate the technical disadvantages of the prior art, by providing a device and a method for controlling the intra-abdominal fat that should allow measuring the intra-abdominal fat at a very high rate and that should thereby allow keeping the progressive slimming of the patient under control.

Such measurements should be able to be carried out at a high frequency and regularly over time to allow tracing a curve of intra-abdominal fat loss which is useful for obtaining prognostic information on the patient's health.

Another object of the invention is to provide a device and a method for measuring intra-abdominal fat which does not require complex radiological and ultrasound systems.

Last but not least, another object of the invention is to provide a device and a method for monitoring the extent of intra-abdominal fat which should not have harmful effects on the patient even when carried out in high number.

SUMMARY OF THE INVENTION

These and other objects of the present invention are achieved in a device for monitoring or measuring intra-abdominal fat in the course of monitoring an individual's slimming activities, which comprises at least one electrical signal generator connected to at least one first pole, associable to the stomach surface, and a second pole, associable to the abdominal wall, said poles being connected to detection means and means for processing said electrical signals to provide a signal indicating the intra-abdominal fat.

Advantageously, the second pole is associable to the electrical signal generator box, or pacemaker, arranged on the outside of the abdominal wall.

The electrical circuit is closed by the tissue between the first and the second pole which, in an obese individual will comprise a considerable component of intra-abdominal fat.

Therefore, the impedance analysis upon the passage of an electrical pulse in this circuit provides an indication of the extent of intra-abdominal fat.

The invention also relates to a method for determining the extent of intra-abdominal fat in the monitoring of an individuals slimming, wherein the impedance of abdominal fat tissues is measured, and from the measured impedance the extent of intra-abdominal fat is obtained.

Advantageously, impedance is measured between the two poles of an electrical circuit.

Advantageously, the device and the procedure can comprise elements such as an electro-catheter and stimulator (pacemaker) that have been implanted in the patient for treating obesity and stomach motor disorders.

BRIEF DESCRIPTION OF TH DRAWING

Figure 2:
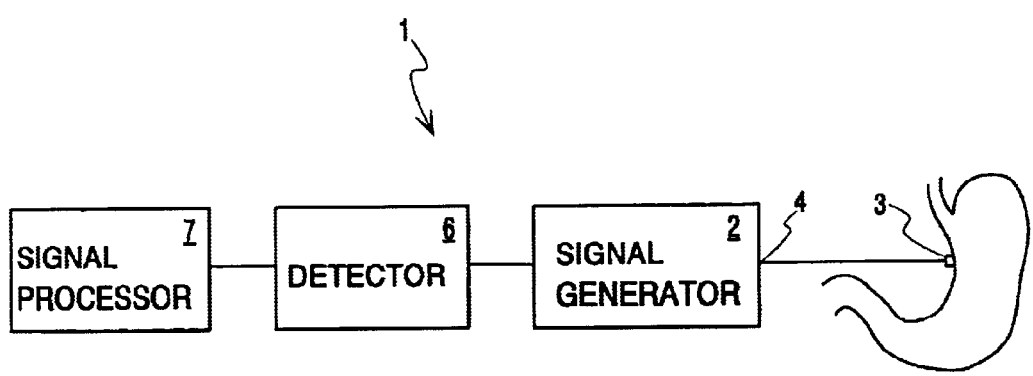

Further features and advantages of the invention will appear more clearly from the description of a preferred but non-exclusive embodiment of the device and method for determining controlling the extent of intra-abdominal fat according to the invention, where the device is illustrated in the accompanying drawing. In the drawing:

FIG. 1 is a schematic view of a device according to the invention, applied to a patient; and FIG. 2 shows a schematic section of a device according to the invention applied to a patient.

SPECIFIC DESCRIPTION

The drawing shows a device for determining the extent of intra-abdominal fat in the monitoring of an individual's slimming program, indicated as a whole reference numeral 1.

Device 1 comprises an electrical signal generator 2 connected to at least one first pole 3 associable to the stomach surface, and a second pole 4, associable to the abdominal wall in a super-fascial position.

Pole 3 is a component of an electro-catheter 5, whereas pole 4 in FIG. 1 consists of a portion of the signal generator, whereas in FIG. 2 it can be a component of electrocatheter 5.

In practice, poles 3 and 4 are arranged at opposed sides of the intra-abdominal adipose layer that must be measured (to check the extent of intra-abdominal fat).

The two poles 3 and 4 are reciprocally connected through detection means 6 and means for processing electrical signals 7 intended to provide an indicative signal of the extent of intra-abdominal fat.

The detection means 6 comprises, for example, a wand or a knob of electromagnetic signals, and the means for processing electrical signals 7 comprises a laptop or computer (electronic processor).

Wand 6 is connected to laptop 7 for communicating with a microchip of the signal generator or pacemaker, and the laptop supports a suitable program for managing communication with access to the data being measured.

Advantageously, the electrical signal generator 2 is intended to generate pulse signals (pacemaker).

In a first embodiment, the second pole 4 comprises at least one portion of the electrical signal generator or pacemaker 2 and the first pole 3 comprises an electrode of electro-catheter 5.

The electrical signal generator 2 (pacemaker) and electrocatheter 5 can be the same used for the electrical stimulation of the stomach, thereby no further surgical intervention is needed besides that for implanting the gastric pacemaker 2 for treating obesity and the motor disorders of the stomach.

Device 1 realized according to this embodiment is especially suitable to be implanted for measuring the extent of intraabdominal fat after an implantation of a gastric electrocatheter connected to an electrical signal generator.

In a different embodiment, the second pole 4 comprises an outside subcutaneous detector and the first pole 3 comprises at least one electrode of electro-catheter 5. Device 1 realized according to this embodiment is especially suitable to be implanted for controlling the extent of fat after a bariatric surgery for treating obesity.

Advantageously, the detection means 6 of device 1 is intended to measure the impedance of abdominal fat tissues, and the processing means 7 is intended to indicate the extent of intra-abdominal fat.

Preferably, the detection means 6 is intended to detect the voltage (potential difference) between abdominal tissues when the same are traversed by a predetermined current.

The operation of the device for controlling the extent of intra-abdominal fat according to the invention is evident from what has been described and illustrated, and in particular, it substantially is as follows.

The operation is based on the principle that biological tissues have a certain impedance upon the passage of electrical current, which varies according to the extent of the different proportions between lean mass, adipose tissue and liquids of which they are composed.

Thus, when stimulator 2 generates an electrical signal, it circulates in the electro-catheter 5 up to the first pole 3, crosses the tissue containing also the adipose component (of course predominant in obese individuals) and reaches the second pole 4.

During the queries of the signal generator or pacemaker (generally on a monthly, three-monthly or annual basis), a single-pole signal is generated to test the tissue impedance. A dedicated software stores the obtained values to the signal generator or pacemaker memory, and provides a graph on a fixed number of months.

The query/programming of the signal generator or pacemaker occurs through electromagnetic pulses provided by an outside WAND.

The detection means 6 detects the potential difference across the adipose tissue and thus, based on the known Ohm law ($V = R \times i$, where V is the potential difference across the intra-abdominal adipose tissue, R is the impedance of body tissues, and i is the current passing through the biological tissues between the two poles), the impedance R of the intra-abdominal adipose layer is obtained.

From the impedance value R the processing means is capable of obtaining the extent of endo-abdominal fat since, as known, the biological tissue exhibits a given impedance upon the passage of an electrical current, which varies according to the different amount of fat contained therein.

The present invention also relates to a method for determining the extent of intra-abdominal fat.

The method according to the invention consists in measuring the impedance of abdominal adipose tissues and hence, obtaining the extent of intra-abdominal fat.

Impedance is measured by making a predetermined current pass through the abdominal tissues and measuring the voltage across between abdominal tissues.

Preferably, impedance is measured between the stomach surface and the abdomen wall.

Moreover, the procedure provides for the preliminary application of an electrical signal generator 2 (pacemaker) in super-fascial position.

In the practice, it has been proved that the device and method for determining the extent of intra-abdominal fat in the monitoring of an individual's slimming according to the invention, are especially advantageous since they allow tracing a curve of endo-abdominal fat loss, which has a considerable prognostic importance on the patient's health.

The device and procedure for controlling the extent of intra-abdominal fat in the monitoring of an individual's slimming thus conceived can be subject to several variants and changes, all falling within the scope of the inventive idea; moreover, all details can be replaced with other technically equivalent elements.

In the practice, the materials used as well as the sizes, can be of any type according to the needs and to the state of the art.

What is claimed is:

1. A device for determining intra-abdominal fat of a person, comprising:
   a gastric pacemaker for producing electrical pulses capable of stomach stimulation in a treatment of obesity, said pacemaker having a first electrical pole attachable at a stomach wall of the person and a second electrical pole attachable in subcutaneous tissue of an abdominal wall of the person in a supra-fascial position, whereby electrical pulses produced by the gastric pacemaker traverse adipose tissue of the person;
   a detector connected to said poles for detecting an electrical signal representing an amount of adipose tissue between said poles; and
   a signal processor connected to said detector for indicating said amount of adipose tissue from the electrical signal detected by said detector.

2. The device defined in claim 1 wherein one of said poles is formed by a portion of an electrical pulse generator of said pacemaker producing said electrical pulses.

3. The device defined in claim 1 wherein one of said poles is formed on a catheter.

4. The device defined in claim 1 wherein said detector is constructed and arranged to measure a voltage across said poles.

5. A method of determining intra-abdominal fat of a person, comprising:
   installing in the body of the person a gastric pacemaker for producing electrical pulses capable of stomach stimulation in a treatment of obesity, said pacemaker having a first electrical pole at a stomach wall of the person and a second electrical pole in subcutaneous tissue of an abdominal wall of the person in a supra-fascial position, whereby electrical pulses produced by the gastric pacemaker traverse adipose tissue of the person;
   detecting an electrical signal representing an amount of adipose tissue between said poles with a detector connected to said poles; and
   processing said electrical signal with a signal processor connected to said detector for indicating said amount of adipose tissue from the electrical signal detected by said detector.

6. The method defined in claim 5 wherein the amount of adipose tissue is plotted in a graph over a period of months.

7. The method defined in claim 5 wherein the detected electrical signal is a voltage.

* * * * *